(12) United States Patent
Chan et al.

(10) Patent No.: US 11,712,178 B2
(45) Date of Patent: Aug. 1, 2023

(54) PLANTAR PRESSURE SENSING SYSTEM

(71) Applicant: CHANG GUNG UNIVERSITY, Taoyuan (TW)

(72) Inventors: Hsiao-Lung Chan, Taipei (TW);
Jiunn-Woei Liaw, Taoyuan (TW);
Ya-Ju Chang, Taoyuan (TW);
Cheng-Chung Kuo, Taoyuan (TW)

(73) Assignee: CHANG GUNG UNIVERSITY, Taoyuan (TW)

( * ) Notice: Subject to any disclaimer, the term of this patent is extended or adjusted under 35 U.S.C. 154(b) by 162 days.

(21) Appl. No.: 17/220,229

(22) Filed: Apr. 1, 2021

(65) Prior Publication Data
US 2021/0307646 A1    Oct. 7, 2021

(30) Foreign Application Priority Data

Apr. 6, 2020    (TW) .................................. 109111433

(51) Int. Cl.
*G01L 5/00*        (2006.01)
*A61B 5/103*       (2006.01)
*A61B 5/00*        (2006.01)

(52) U.S. Cl.
CPC .......... *A61B 5/1038* (2013.01); *A61B 5/6807* (2013.01); *G01L 5/0052* (2013.01); *A61B 2562/0247* (2013.01); *A61B 2562/046* (2013.01)

(58) Field of Classification Search
CPC ................ A61B 5/1038; A61B 5/6807; A61B 2562/0247; A61B 2562/046; G01L 5/0052
See application file for complete search history.

(56) References Cited

U.S. PATENT DOCUMENTS

| 2009/0234259 | A1* | 9/2009 | Hardman | ............. | A61B 5/0002 601/134 |
| 2012/0014637 | A1* | 1/2012 | Hishida | ................. | G01L 5/0052 385/12 |
| 2014/0326085 | A1* | 11/2014 | Lee | ........................ | A61B 5/112 73/865.4 |
| 2018/0008817 | A1* | 1/2018 | Ejiri | ...................... | A61B 5/6807 |
| 2018/0274996 | A1* | 9/2018 | Rice | ................... | A63B 24/0062 |
| 2020/0245906 | A1* | 8/2020 | Yang | .................... | G02B 3/0056 |
| 2021/0405802 | A1* | 12/2021 | Guo | ..................... | G06F 3/04144 |

* cited by examiner

*Primary Examiner* — Max H Noori
*Assistant Examiner* — Masoud H Noori
(74) *Attorney, Agent, or Firm* — Cheng-Ju Chiang

(57) ABSTRACT

A plantar pressure sensing system is located at a sole of shoe. The plantar pressure sensing system includes a first layer, a second layer a plurality of sensor, a plurality of convex portions, a plurality of connection portions, a processor and a storage. The processor is coupled with the storage and configured to be connected with the plurality of sensors. The plurality of sensors are configured to form the first layer. The plurality of convex portions and the plurality of connection portions are configured to form the second layer. Overall, the plantar pressure sensing system is able to detect pressure with the sensors by setting the alignment of the convex portions, thereby obtaining a more accurate pressure(s) reading from the sole of shoe. The data validity of the plantar pressure sensing system is improved.

10 Claims, 2 Drawing Sheets

PLANTAR PRESSURE SENSING SYSTEM

TECHNICAL FIELD

The present invention relates to a kind of sensing system, especially a sensing system to detect the plantar pressure.

DESCRIPTION OF THE RELATED ART

In recent years, with the increasing popularity of auxiliary gait performance correction devices, it is more and more common to install sensors inside (or at the bottom) of shoes. Usually, the sensor detects the pressure value of the human foot to enhance gait function and activities or improve the collection of detected information. Generally speaking, the accuracy of the gait performance test is related to the number of sensors; that is, the more sensors there are, the easier it is to obtain information close to the exact gait performance. However, based on cost considerations, there is only a single sensor set at the heel position in most of the relevant products currently on the market. Therefore, when the user requires more complete correction or detected information (such as assisting people with physical disabilities to perform gait training), the aforementioned products don't exactly meet the needs and remains to be improved.

In addition, while a small number of products set the sensor according to the needs of users, they cannot be popularized because there is no related configuration logic (that is, the operating specifications). Among them, products that can be popularized are usually achieved by using sensors on the soles of the shoes, but the cost of such products is more expensive, and it is not affordable for general users.

SUMMARY

In order to solve the abovementioned problems, some embodiments of the present invention provide a sensing system, in particular a sensing system for foot pressure sensing, taking advantage of being able to calculate the pressure of the sole accurately and in real time. Specifically, it utilizes the alignment setting of the convex portions to assist the sensors in pressure detection, therefore more accurate pressure readings can be obtained. As a result, the data validity of the system is improved.

In order to achieve the above purpose, the present invention discloses a plantar pressure sensing system, disposed at a sole of a shoe, wherein the sole comprising at least one first layer and at least one second layer; wherein the plantar pressure sensing system comprising: a plurality of sensors, a plurality of convex portions, a plurality of connection portions, at least one processor, and at least one storage; wherein the at least one processor connects with the at least one storage, and both are configured to connect to the plurality of sensors; wherein the plurality of sensors are configured to form the at least one first layer; wherein the plurality of convex portions joined with the connection portions and both are configured to form the at least one second layer disposed above or beneath the at least one first layer.

At least one embodiment of the present invention is characterized by a segmentation procedure of the plantar pressure sensing system. In some cases, in order to more accurately define the foot position requires to be calculated, the system further includes: a plurality of regions, any of which is divided from the at least one first layer and the at least one second layer, and the plurality of regions at least comprise any one of the convex portions and any one of the sensors aligned therewith.

The above summary of the present disclosure is to provide a basic description of the various aspects and features of the present disclosure. It is not a detailed description. Its purpose is not to specifically recite keys or critical elements of the present disclosure, and it is not intended to limit the scope of the present disclosure. It merely presents a few concepts of the present disclosure in a concise manner.

DESCRIPTION OF THE PREFERRED EMBODIMENTS

To clarify the purpose, technical solutions, and the advantages of the disclosure, embodiments of the present disclosure will now be described more fully hereinafter with reference to the accompanying drawings.

The present invention relates to a kind of sensing system, especially a sensing system to detect the plantar pressure.

Figure 1:
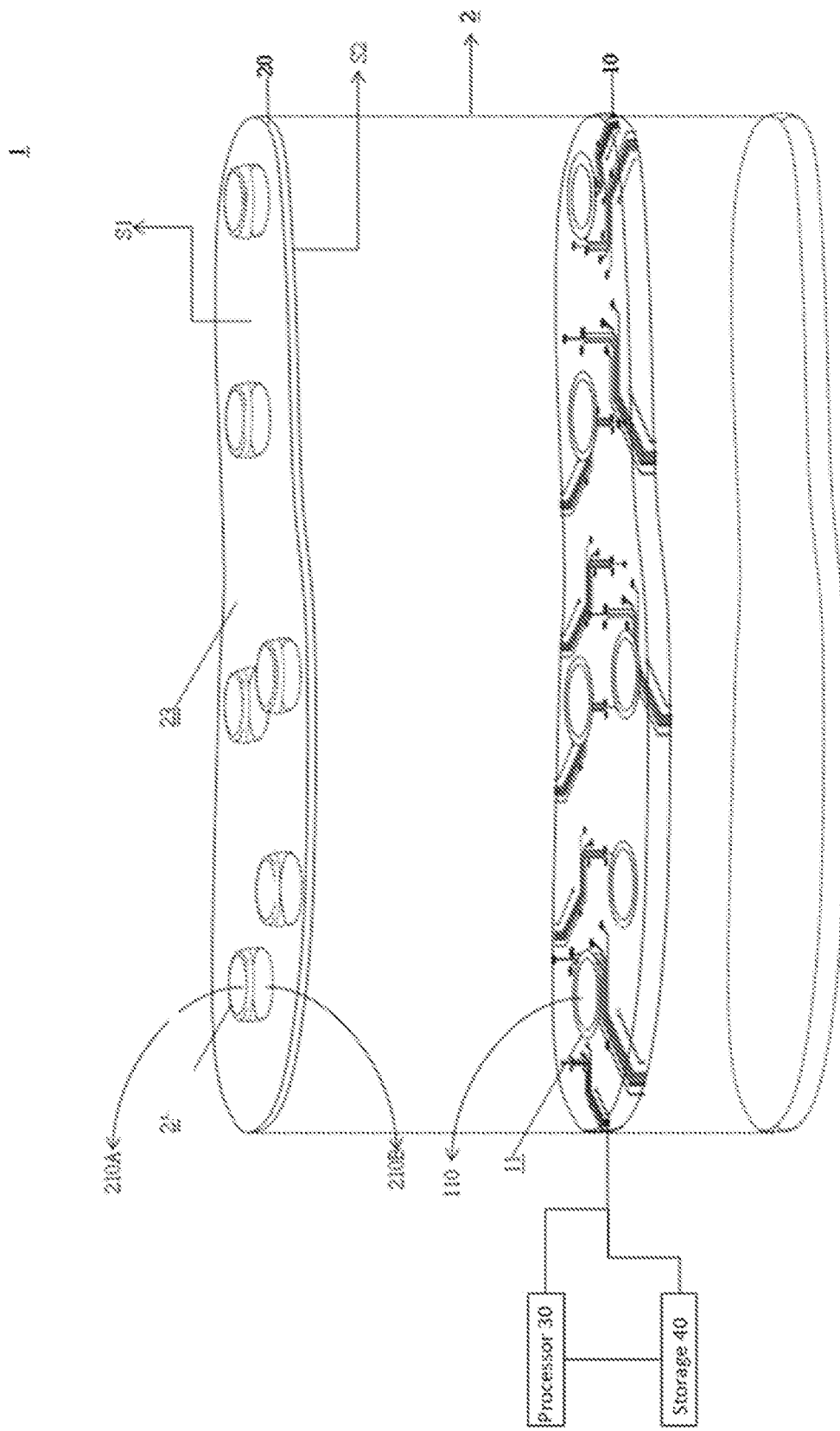
FIG. 1 is a diagram illustrating the plantar pressure sensing system in accordance with one embodiment of the present disclosure.

Please refer to FIG. 1. FIG. 1 is a schematic diagram of some embodiments of the foot pressure sensing system of the present invention. The foot pressure sensing system 1 of this embodiment is disposed on a sole 2 and includes a plurality of sensors 11, a plurality of convex portions 21, a plurality of connecting portions 23, at least one processor 30 and at least one storage 40. The processor 30 is connected to the storage 40 and configured to connect to the sensors 11. The sensors 11 are configured to form at least one first layer 10 of the sole 2, and the convex portions 21 and the connecting portions 23 are configured to form the at least one second layer 20 above the first layer 10. Hereinafter, for the ease of description, it will be assumed that the second layer 20 is located above the first layer 10 as shown in FIG. 1. In addition to this configuration, the present invention can also set the at least one second layer 20 below the first layer 10 or both above and below the first layer 10 (that is, in the case that the number of the second layers 20 are plural) according to the requirements.

In FIG. 1, each convex portion 21 aligns with at least part of a sensor 11. In this embodiment, said sensor 11 may be a resistive pressure sensor (such as a Varistor or a Force Sensing Resistor), Capacitive Pressure Sensor or Strain Gauge (SG) sensor to provide pressure readings from the plantar of the sole 2. For example, A201 Single point pressure sensor provided by G-CHEN Technology corporation or FlexiForce® A201 piezoresistive force sensor provided by MEMS Technology corporation may be alternative choices. It should be noticed that the sensor 11 in the present invention is not limited to the pressure sensor as used in this embodiment. In other practical applications, other types of sensors (such as gyroscopes or acceleration sensors) may also be utilized in combination to assist in providing different exercise readings, such as step count, walking time or other test readings.

Moreover, the number of the aforementioned sensors 11 is not limited in the embodiment, and the specific number can be preferably selected according to the size of the shoe sole 2. In addition, in the following embodiments, it will be assumed that the number of the sensors 11 is any number larger than one for obtaining pressure readings at different positions of the sole of the foot when the sole 2 is touched. In this way, the processor 30 could obtain the plantar center of gravity at different time points only by estimating the pressure readings. Then, people are allowed to draw a path diagram (such as a center-of-gravity path diagram) or provide evaluation parameters (such as a standard deviation and/or angle of center-of-gravity shift) based on the plantar center of gravity. The present embodiment disclosed is only one of the examples, and the purpose of the pressure reading is not intended to be limited to the precise forms disclosed.

As shown in FIG. 1, the processors 30 of the present embodiment are set in or around the sole 2, therefore to connect more than one sensors 11 by wire and/or wireless way, obtaining the different detection readings (i.e., pressure readings) when pressing different positions of the shoe sole 2. The arrangement of the position of the processor 30 is not limited to the example shown in FIG. 1. For example, the processor 30 can also be arranged on the position of the shoe sole 2 corresponding to the groove of the foot arch. Specifically, the processor 30 is designed to generate the at least one second signal in response to the pressure of the sole 2 based on the at least one first signal output by the sensor 11. In this case, the first signal refers to an electrical signal of the sensor 11 produced by the amount of pressure applied on the sole 2 of the shoe; and the second signal indicates the corresponding pressure reading produced from the above electrical signal. During processing, the processor 30 will be configured to acquire the data related to the operation (such as pressure readings or detection readings, etc.) which is stored in and/or retrieved from the storage 40. Noticeably, although the models and/or types of the processor 30 and the storage 40 are not clearly defined here, those skilled in the art will easily understand that the processor 30 in FIG. 1 may be any processor, control unit, device or other combination or configuration of components for realizing computing, such as a microcontroller (microcontroller Unit, MCU) or a microprocessor (Central Processing Unit, CPU). Likewise, the storage 40 can be any type of fixed or portable storage, which is configured to store any type of information that the processor 30 may require.

In addition, the processor 30 as shown in FIG. 1 obtains the first signal by setting a wired and/or wireless connection with the sensor 11 for practical application. Exemplary wired connections include any physical communication connections with cables (such as copper wires or cables); in addition, exemplary wireless connections include Bluetooth®, Wi-Fi, radio frequency (RF) or infrared virtual communication connection. And in operation, the sensor 11 optionally stores the first signal in the storage 40 and/or directly sends the first signal to the processor 30 to form the second signal.

In FIG. 1, the second layer 20 is disposed on the first layer 10 formed by the sensors 11. When no pressure is applied (that is, when the plantar does not touch the sole 2), the second layer 20 will remain in the state of no contact with the first layer 10. Under temporary pressure (i.e., in the case of foot touching sole 2), the second layer 20 will be able to access the sensor 11 of the first layer 10 through the aforementioned convex portions 21. In this embodiment, the setting of the convex portions 21 is performed by aligning it with the specific pressure sensor in the sensor 11, preferably by aligning a single convex portion 21 with a single pressure sensor 11. Simultaneously, the convex portions 21 is connected to other adjacent convex portions 21 via the flat connecting portion 23. It is worth mentioning that in the practical application of the present invention, the convex portions 21 can be made of any suitable material or combination of materials, such as but not limited to polyurethane (PU), polystyrene (PS), polyethylene (PE), polypropylene (PP), ethylene-vinyl acetate copolymer (EVA), expanded polyethylene (EPE), expanded polystyrene (EPS), etc. Meanwhile, the hardness of the convex portion 21 must be sufficient to make the first signal of the output of the pressure sensor 11 not less than a preset threshold. On the other hand, the preset threshold may be programmed by the user and designed with the sensitivity of the pressure sensor in the sensor 11, the present invention is not limited. The connecting portion 23 is able to be made of the materials exemplified above, which are the same as the convex portion 21, but also could be composed of other suitable materials, such as but not limited to ethylene propylene diene rubber (EPDM), chloroprene rubber (CR), nitrile Rubber (NBR), etc. In fact, a concave-convex structure can be given by processing depending on the practical application.

As mentioned previously, when said materials (i.e. said materials are selected from the total materials of convex portions 21 and connection portions 23 exemplified above) are used to form the second layer 20 as shown in FIG. 1, the softness of the various parts of the second layer 20 can be designed according to the requirements. For example, the part of the second layer 20 corresponding with the foot heel part is relatively soft to increase the comfort; otherwise, the part of the second layer 20 corresponding with the foot bow part is relatively hard to increase the support function.

It should be noticed that the embodiment of FIG. 1 assumes that the convex portions 21 and the connection portions 23 are set to the same plane, and that either the first surface S1 or the second surface S2 of the second layer 20 is approximately flat. In this embodiment, the surface of the convex portion 21 facing the first layer 10 in FIG. 1 is defined as the bottom surface 210B, and the other surface of the convex portion 21 is the top surface 210A. That is, the top surface 210A is flat in this embodiment. Accordingly, the top surface 210A of each convex portion 21 is flush with each connecting portion 23, joined with the adjacent convex portions 21 with connecting portion 23 to form the second layer 20. In this embodiment, the convex portions 21 protrude downward from the second layer 20. The protruding part of the convex portions 21 touches the aforementioned sensor 11 via the bottom surface 210B. However, the possible arrangement of the convex portion 21 and the connecting portion 23 are not limited in the previous embodiment. For example, when the convex portion 21 protrude upward from the second layer 20 (that is, the bottom surface 210B is flush with the connecting portion 23), the convex portion 21 will be directly/indirectly pressed on the top surface 210A through the plantar, so that the bottom surface 210B is able to touch the sensor 11. For another example, when the convex portion 21 protrudes upward and downward from the second layer 20 (that is, when the top surface 210A and the bottom surface 210B are flush with the connecting portion 23 at the same time), the bottom surface 210B in this embodiment is able to help ensuring the two-sided contact with the sensor 11. The "protrudes upward and downward from the second layer 20" mentioned previously indicates that the convex portion 21 is flat with respect to the surface of the second layer 20 (the first surface S1 or the second surface S2) and relatively extends from the second layer 20 on both sides. Additionally, the size of each convex portion 21 may vary depending on the relative formed shape (for example, the size of the convex portion of the upper convex shape is larger than the size of the convex portion of the lower convex shape, etc.).

The foregoing description is only one of the embodiments, and does not limit the scope of the present invention. For example, each of the convex portions 21 and each of the connecting portions 23 can also be arranged on different planes to further enhance the accuracy of the convex portion 21 pressing the sensor 11.

On the other hand, the convex portion 21 of the present invention may be in various shapes (such as a circular shape, an elliptical shape, or a rectangular shape) and be integrally formed with the connecting portion 23 in one piece for the second layer 20 (for example, through three-dimensional printing (3D printing)). Otherwise, the convex portion 21 may be separately molded and joined to the connecting portion 23 to form the second layer 20. In this way, when only part of the foot (e.g., the heel) exactly touches the sole 2, the convex portion 21 helps the part of the sole that fails to definitely touch the sole 2. The "the foot exactly touches the sole 2" means that the movement of the second layer 20 touching the first layer 10 based on the direct/indirect suppression of the foot. Meanwhile, each sensor 11 (pressure sensor) constituting the first layer 10 has been pressed by the convex portion 21 or the connecting portion 23, which render the first layer 10 in a flattened state. The flattened state of the first layer in different level produces the first signal as defined previously. Then, the first signal at this time will be able to more accurately present the plantar pressure. Moreover, with the aforementioned method (integrated molding/single molding) in practical applications, the convex portion 21 and/or the connecting portion 23 can also be composed of a plurality of separate parts. Filling the gas between the separate parts (i.e., air) forms the at least one air part. The at least one air part helps the sensor 11 of the first layer 10 to sense the pressure produced. In this way, the convex portion 21 and/or the connecting portion 23 will not be limited to a solid structure, thereby reducing the material cost.

Please refer to FIG. 1. In this embodiment, each of the sensors 11 (pressure sensor) includes a sensing surface 110, which is aligned with each of the convex portion 21, preferably is aligned with each of the bottom surface 210B of the convex portion 21. As viewed in plan, the shape of the sensing surface 110 is a circular shape, or may be any shape such as a polygon, an ellipse, a rectangle and it is not intended to limit the scope of the present invention. In addition, following the foregoing description, the shape of the sensing surface 110 can also be the same as that of the convex portion 21. In this way, the increased contact area between the convex portion 21 and the sensing surface 110 will enable the sole to exert more uniform pressure on the sole 2. That is, the pressure is distributed over the entire sensing surface 110 to acquire more uniform pressure on the sensing surface 110. In addition, the shape of the sensing surface 110 may only be the same as the bottom surface 210B of the convex portion 21, and in this case, the shape of other parts of the convex portion 21 can be any shape, as long as it assures the first signal is not lower than the aforementioned preset threshold.

Figure 2:
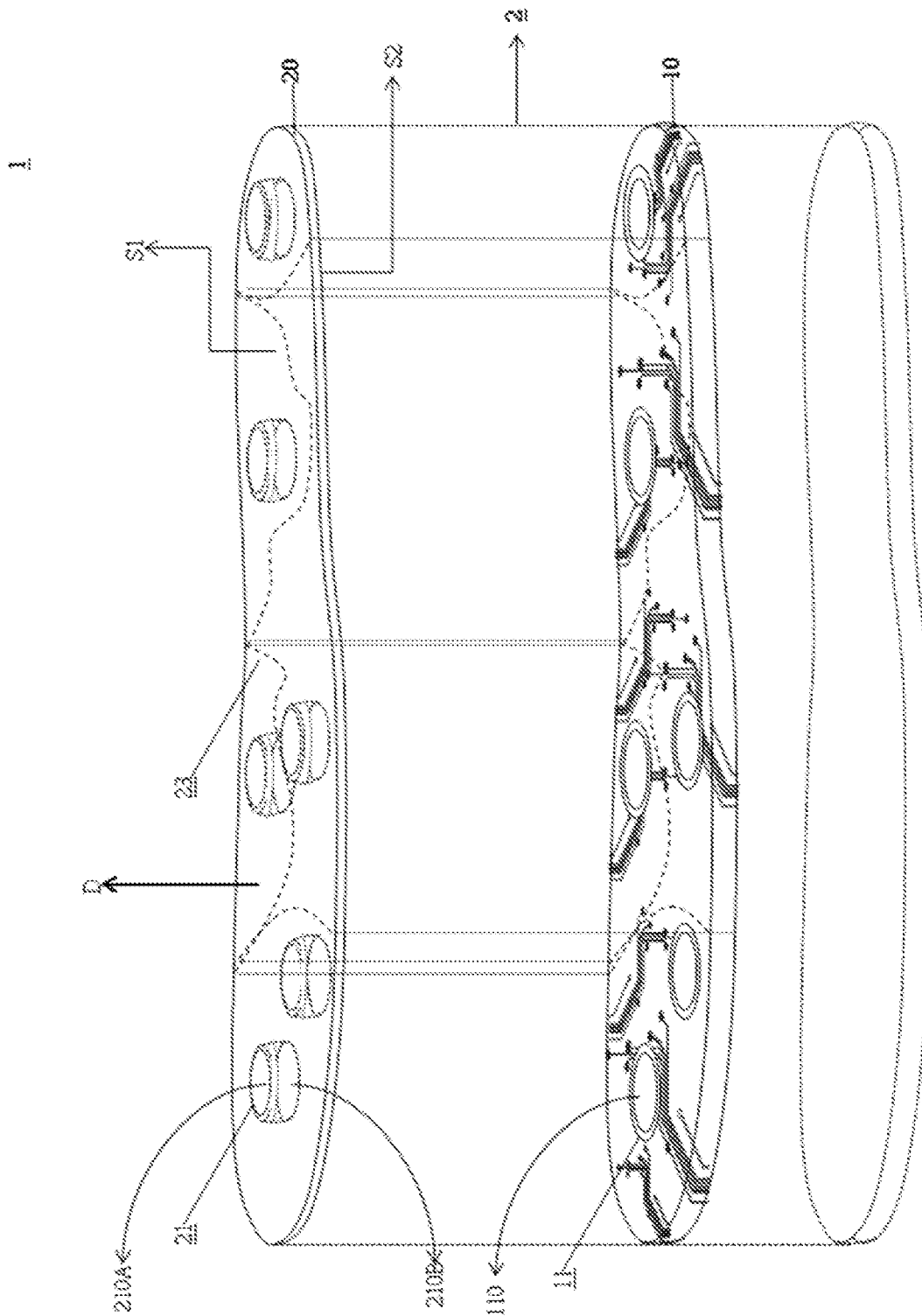
FIG. 2 is a diagram illustrating the plantar pressure sensing system in accordance with another embodiment of the present disclosure.

Please refer to FIG. 2, which is another schematic diagram of some embodiments of the plantar pressure sensing system 1 of the present invention. The sensors 11 (pressure sensors) in FIG. 2 may be connected in series and/or in parallel to adjust the basis for generating the aforementioned first signal according to the requirements and designs for practical application. As such, the number of sensors 11 used in the present invention could be smaller than that of the prior arts. Specifically, where the sensors 11 are connected in parallel (i.e., Force Sensing Resistor (FSR)), the basis may be the electrical impedance change between the sensors 11; where the sensors 11 are connected in series (i.e., Strain gauge (SG)), the basis may also be the sum of the pressure changes of the sensors 11. The "the requirements and designs for practical application" here includes the completion of the pre-actions that are determined to be performed in series and/or parallel based on the electrical specifications of each sensor 11.

In application, the distribution design of the aforementioned first layer 10 and the aforementioned second layer 20 can be divided into a plurality of regions D according to requirements. Each region D includes at least one convex portion 21 and a corresponding sensor 11 aligned with it. 11 (pressure sensor). When the number of sensor 11 is plural, the sensors 11 are connected in series and/or in parallel. It is worth mentioning that when the second layer 20 is located above and below the first layer 10, each Area D of the different second layer 20 can be set to be completely non-overlapping, partially overlapping or completely overlapping, which could be adjusted depending on the type of the sensors 11. It should be noted that the "distribution design" mentioned here can be based on the user's own information (e.g., Center Of Pressure, foot clearance, or Foor Progression Angle); or it can also be performed based on the trained prediction model of the big data database. To be more specific, the number of "Area D" here can also be increased or decreased based on application requirements (i.e., the number of Area D can be between 2 to 16; preferably 4 to 16), the present invention is not limited.

Moreover, in other applications of the present invention, the number of the first layer 10 and/or the second layer 20 can also be plural, and in this case, the second layer 20 can be overlapped above or below the first layer 10 respectively, or both above and below the first layer 10.

The above description is merely the embodiments in the present disclosure, the claim is not limited to the description thereby. The equivalent structure or changing of the process of the content of the description and the figures, or to implement to other technical field directly or indirectly should be included in the claim. All other embodiments obtained by a person of ordinary skill in the art based on the embodiments of the present disclosure without creative efforts shall fall within the protection scope of the present disclosure.

What is claimed is:

1. A plantar pressure sensing system, disposed at a sole of a shoe, wherein the sole comprising at least one first layer and at least one second layer;

wherein the plantar pressure sensing system comprising:
- a plurality of sensors, configured to form the at least one first layer;
- a plurality of convex portions joined with connection portions, configured to form the at least one second layer;
- at least one processor, configured to connect to the plurality of sensors;
- wherein at least one second signal is produced in response with pressure from the sole based on at least one first signal produced from the sensor; and
- at least one storage, connected with the at least one processor;
- wherein the at least one second layer is disposed above or beneath the at least one first layer;

wherein any one of the convex portions is aligned with at least a part of the plurality of sensors.

2. The plantar pressure sensing system as claimed in claim 1, wherein the at least one second layer is plural, the plural second layers are respectively located above and below the at least one first layer.

3. The plantar pressure sensing system as claimed in claim 1, wherein the at least a part of the plurality of sensors are pressure sensors, and the pressure sensor comprises a sensing surface, and wherein any one of the convex portions is configured to align with any one of the sensing surfaces.

4. The plantar pressure sensing system as claimed in claim 1, wherein the at least one second layer includes a first surface and a second surface, and the plurality of convex portions are configured to protrude and form on at least a part of the first surface or the second surface.

5. The plantar pressure sensing system as claimed in claim 1, wherein any one of the convex portions is joined to the adjacent plurality of convex portions via the plurality of connection portions.

6. The plantar pressure sensing system as claimed in claim 1, wherein the at least one first layer and the at least one second layer are correspondingly divided into a plurality of regions, and any one of the plurality of regions includes at least any one of the convex portions and any one of the sensors aligned therewith.

7. The plantar pressure sensing system as claimed in claim 3, wherein any one of the convex portions further comprises a top surface, and wherein the at least one second layer is pressed, the top surface touches the sensing surface.

8. The plantar pressure sensing system as claimed in claim 3, wherein any one of the convex portions further comprises a bottom surface, and wherein the at least one second layer is pressed, the bottom surface touches the sensing surface.

9. The plantar pressure sensing system as claimed in claim 3, wherein the shape of any one of the convex portions corresponds to the shape of any one of the sensing surfaces at the same position.

10. The plantar pressure sensing system as claimed in claim 6, wherein the plurality of sensors in any of the plurality of areas are connected in parallel or in series.

* * * * *